(12) United States Patent
Jungong et al.

(10) Patent No.: US 10,875,819 B2
(45) Date of Patent: Dec. 29, 2020

(54) PROCESSES FOR PRODUCING TRIFLUOROIODOMETHANE USING METAL TRIFLUOROACETATES

(71) Applicant: Honeywell International Inc., Morris Plains, NJ (US)

(72) Inventors: Christian Jungong, Depew, NY (US); Haiyou Wang, Amherst, NY (US); Terris Yang, East Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/797,677

(22) Filed: Feb. 21, 2020

(65) Prior Publication Data

US 2020/0283360 A1  Sep. 10, 2020

Related U.S. Application Data

(60) Provisional application No. 62/813,499, filed on Mar. 4, 2019.

(51) Int. Cl.
*C07C 17/363* (2006.01)
*C07C 17/093* (2006.01)
*C07C 19/16* (2006.01)

(52) U.S. Cl.
CPC .......... *C07C 17/363* (2013.01); *C07C 17/093* (2013.01); *C07C 19/16* (2013.01)

(58) Field of Classification Search
CPC ...... C07C 17/363; C07C 17/093; C07C 19/16
See application file for complete search history.

(56) References Cited

U.S. PATENT DOCUMENTS

| 5,892,091 A | 4/1999 | Harada et al. |
| 2008/0108854 A1 | 5/2008 | Yang et al. |

FOREIGN PATENT DOCUMENTS

| CN | 102992943 | * | 3/2013 | ........... C07C 17/363 |
| EP | 0375920 A1 | | 7/1990 | |

OTHER PUBLICATIONS

Haszeldine, R. N. (1951). 124. The Reactions of Metallic Salts of Acids with Halogens. Part I. The Reaction of Metal Trifluoroacetates with Iodine, Bromine, and Chlorine. Journal of the Chemical Society, pp. 584-587.
International Search Report and Written Opinion received for PCT Patent Application No. PCT/US2020/020256, dated Jun. 25, 2020, 11 pages.

* cited by examiner

*Primary Examiner* — Jafar F Parsa
(74) *Attorney, Agent, or Firm* — Faegre Drinker Biddle & Reath LLP

(57) ABSTRACT

The present disclosure provides a process for producing trifluoroiodomethane. The process includes providing a metal trifluoroacetate, iodine, a phase transfer catalyst, and an organic solvent, and reacting the metal trifluoroacetate and iodine in the presence of the phase transfer catalyst and the organic solvent to produce trifluoroiodomethane.

20 Claims, 1 Drawing Sheet

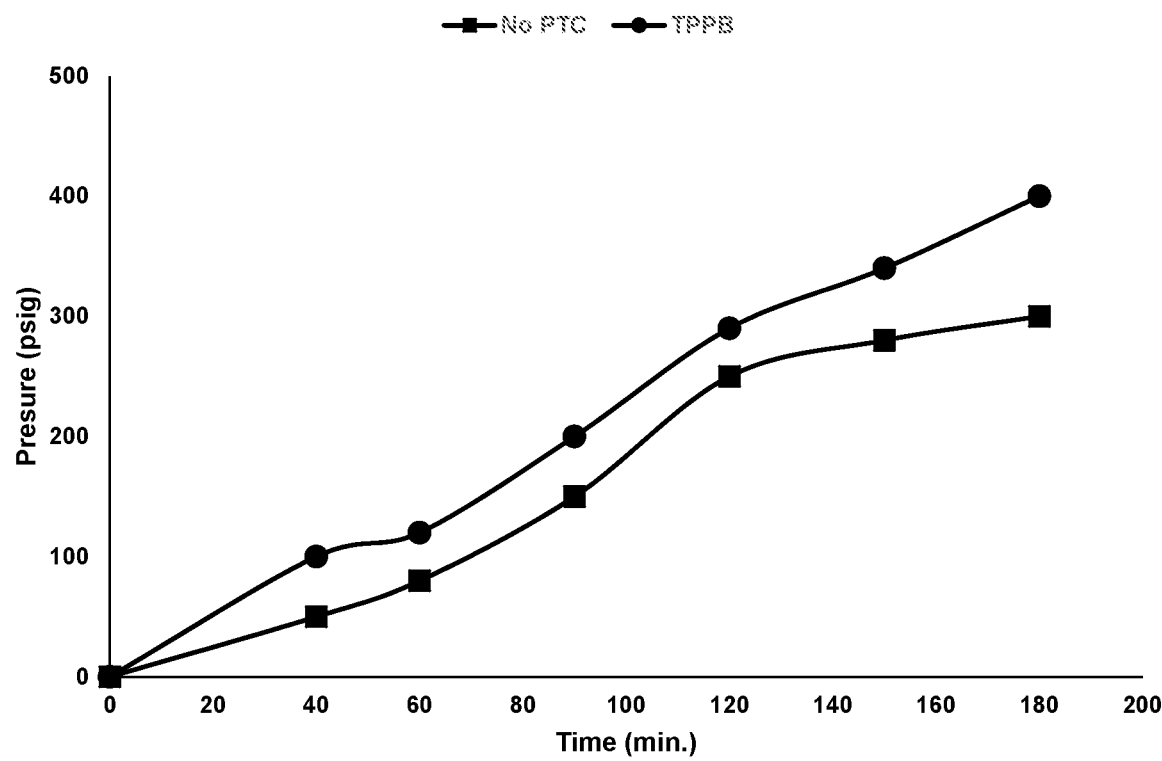

PROCESSES FOR PRODUCING TRIFLUOROIODOMETHANE USING METAL TRIFLUOROACETATES

CROSS-REFERENCE TO RELATED APPLICATIONS

This application is a U.S. Nonprovisional Application which claims priority to Provisional Application No. 62/813,499, filed Mar. 4, 2019, which is incorporated herein by reference in its entirety.

FIELD

The present disclosure relates to processes for producing trifluoroiodomethane ($CF_3I$). Specifically, the present disclosure relates to methods to produce trifluoroiodomethane from metal trifluoroacetates in the presence of a phase transfer catalyst.

BACKGROUND

Trifluoroiodomethane ($CF_3I$) is a useful compound in commercial applications, as a refrigerant or a fire suppression agent, for example. Trifluoroiodomethane is an environmentally acceptable compound with a low global warming potential and low ozone depletion potential. Trifluoroiodomethane can replace more environmentally damaging materials.

Methods of preparing trifluoroiodomethane from metal trifluoroacetates and iodine are known. For example, R. N Haszeldine, *Reactions of metallic salts of acids with halogens. Part I. The reaction of metal trifluoroacetates with iodine, bromine, and chlorine*, 124 J. Chem. Soc. 124 (1951) discloses the decarboxylative iodination of metal trifluoroacetates ($CF_3COOM$) in the presence of iodine to make trifluoroiodomethane. The process by R. N Haszeldine is performed in a sealed tube or stainless-steel autoclave in which the metal trifluoroacetate and elemental iodine are heated together in the absence of a solvent to make trifluoroiodomethane. In another example, Chinese Patent CN102992943B discloses the reaction of metal trifluoroacetates and elemental iodine in the liquid phase to produce trifluoroiodomethane, carbon dioxide, and metal iodide.

An intrinsic limitation with the use of metal trifluoroacetates and iodine to make trifluoroiodomethane is that the reaction mixture is heterogeneous as both starting reactants have limited solubility in most organic solvents. The limited solubility of the reactants reduces reaction rate, increases reaction time and manufacturing costs. Therefore, besides the need to develop a process that more efficiently uses iodine, there is also a need to develop a process that allows for increased solubility of metal trifluoroacetates and iodine in the reaction solvent. Improvements in the rate of reaction improve the efficiency of the production of trifluoroiodomethane from metal trifluoroacetates.

SUMMARY

The present disclosure provides processes for producing trifluoroiodomethane by reacting a metal trifluoroacetate with iodine in the presence of a phase transfer catalyst.

In one form thereof, the present disclosure provides a process for producing trifluoroiodomethane. The process includes providing a metal trifluoroacetate, iodine, a phase transfer catalyst, and an organic solvent, and reacting the metal trifluoroacetate and iodine in the presence of the phase transfer catalyst and the organic solvent to produce trifluoroiodomethane.

In one form thereof, the present disclosure provides a process for producing trifluoroiodomethane. The process includes mixing a metal trifluoroacetate, iodine, a phase transfer catalyst, and an organic solvent; and heating the metal trifluoroacetate, iodine, phase transfer catalyst, and the organic solvent to react the metal trifluoroacetate and iodine to produce trifluoroiodomethane and a metal iodide.

The above mentioned and other features of the disclosure, and the manner of attaining them, will become more apparent and will be better understood by reference to the following description of embodiments taken in conjunction with the accompanying drawings.

DESCRIPTION OF THE DRAWING

The FIGURE illustrates the pressure in a reactor versus time for batch syntheses of trifluoroiodomethane corresponding to Examples 1-2 below. The FIGURE compares a synthesis using a phase transfer catalyst to a synthesis without a phase transfer catalyst.

DETAILED DESCRIPTION

The present disclosure provides a liquid phase process for the manufacture of trifluoroiodomethane ($CF_3I$) from metal trifluoroacetate ($CF_3COOM$) and $I_2$ reactants by decarboxylative iodination according to Equation 1 below:

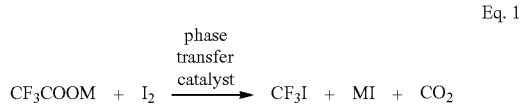

$$CF_3COOM + I_2 \xrightarrow{\text{phase transfer catalyst}} CF_3I + MI + CO_2 \quad \text{Eq. 1}$$

where M may be an alkali metal, such as lithium, potassium, sodium, rubidium, or cesium; an alkaline earth metal, such as calcium or magnesium; or a transition metal, such as iron, zinc, or copper. Thus, the metal trifluoroacetate may include lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, copper trifluoroacetate, or combinations, thereof.

The use of a phase transfer catalyst in the decarboxylative iodination reaction shown above can significantly increase the rate of solvation of reactants in the organic solvents used, directly resulting in an increased reaction rate and decreased reaction time. Phase transfer catalysts can be used to increase the transport of inorganic ions between two mutually-insoluble phases (i.e., liquid-liquid or solid-liquid). The transport of the inorganic ions is achieved by the formation of complexes that are soluble in the organic solvent. The transport of ions into the organic solvent leads to the increase in reaction rate and to the decrease in reaction time which can significantly reduce manufacturing costs. Without wishing to be bound by any theories, it is believed that phase transfer catalysts facilitate movement of reactants from one phase to another in the heterogenous mixture formed by the reactants.

The reaction is carried out in an organic solvent. Organic solvents useful for carrying out the reaction in the liquid phase include dimethylformamide, dimethyl sulfoxide, dimethyl sulfone, N,N-dimethylacetamide, acetonitrile, benzonitrile, N-methyl-2-pyrrolidone (NMP), sulfolane, ionic liquids, and combinations thereof. Examples of ionic liquids include imidazolium salts and caprolactamium hydrogen sulfate.

The solvent is substantially free of water. Substantially free of water means that the amount of water in the solvent is less than about 500 parts per million (ppm), about 300 ppm, about 200 ppm, about 100 ppm, about 50 ppm, about 30 ppm, about 20 ppm, or about 10 ppm, or less than any value defined between any two of the foregoing values. The foregoing ppm values are by weight of the solvent and any water. Preferably, the amount of water in the solvent is less than about 100 ppm. More preferably, the amount of water in the solvent is less than about 50 ppm. Most preferably, the amount of water in the solvent is less than about 10 ppm.

The reaction is carried out in the presence of a phase transfer catalyst. Phase transfer catalysts useful for carrying out the reaction in the liquid phase include quaternary ammonium salts and quaternary phosphonium salts. A non-limiting example of a quaternary ammonium salt is tetramethylammonium chloride. A non-limiting example of a quaternary phosphonium salt is tetraphenylphosphonium bromide. In general, quaternary salts have an affinity for both polar and non-polar reaction media. This property makes it possible for quaternary salts to be used in sub-stoichiometric amounts in two mutually insoluble phases that contain inorganic ionic species. Quaternary ammonium salts are preferred when the reaction temperature is less than 150° C., while quaternary phosphonium salts are preferred when the reaction temperature is greater than 150° C., where decomposition of the quaternary ammonium salt is more likely.

The phase transfer catalyst may be provided for the reaction at a mole percent of the metal trifluoroacetate as low as about 0.5%, about 1%, about 2%, about 5%, about 10%, about 15%, about 20% or about 25%, or as high as about 30%, about 35%, about 40%, about 45%, or about 50%, or within any range defined between any two of the foregoing values, such as about 5% to about 50%, about 2% to about 45%, about 5% to about 40%, about 10% to about 35%, about 15% to about 30%, for example. Preferably, the catalyst is provided at a mole percent of the metal trifluoroacetate from about 0.5% to about 35%. More preferably, the catalyst is provided at a mole percent of the metal trifluoroacetate from about 10% to about 30%. Most preferably, the catalyst is provided at a mole percent of the metal trifluoroacetate from about 20% to about 30%.

Metal trifluoroacetates and iodine are readily available in commercial quantities. For example, potassium trifluoroacetate and iodine may be obtained from Sigma-Aldrich Corp., St. Louis, Mo. The solvents may also be readily obtained in commercial quantities. For example, sulfolane may be also be obtained from Sigma-Aldrich Corp., St. Louis, Mo. The phase transfer catalysts may also be readily obtained in commercial quantities. For example, tetraphenylphosphonium bromide may be obtained from Sigma-Aldrich Corp., St. Louis, Mo.

The reactants may be provided for the reaction at a mole ratio of metal trifluoroacetate to iodine as low as about 0.1:1, about 0.2:1, about 0.3:1, about 0.4:1, about 0.5:1, about 0.6:1, about 0.7:1, about 0.8:1, about 0.9:1, about 0.95:1, about 0.99:1, or about 1:1, or as high as about 1.01:1, about 1.05:1 about, 1.1:1, about 1.2:1, about 1.3:1, about 1.4:1, about 1.5:1, about 1.6:1, about 1.8:1, or about 2.0:1, or within any range defined between any two of the foregoing values, such as about 0.1:1 to about 2.0:1, about 0.5:1 to about 1.5:1, about 0.6:1 to about 1.4:1, about 0.7:1 to about 1.3:1, about 0.8:1 to about 1.2:1, about 0.9:1 to about 1.1:1, about 0.95:1 to about 1.05:1, about 0.99:1 to about 1.01:1, about 1:1 to about 2:1, about 0.8:1 to about 1.5:1, or about 0.95:1 to about 1.2:1, for example. Preferably, the mole ratio of metal trifluoroacetate to iodine is from about 0.8:1 to about 1.5:1. More preferably, the mole ratio of metal trifluoroacetate to iodine is from about 1:1 to about 1.2:1. Most preferably, the mole ratio of metal trifluoroacetate to iodine is about 1:1.

The reaction may be conducted at a temperature as low as about 100° C., about 110° C., about 120° C., about 130° C., about 140° C., about 150° C., about 160° C., or about 170° C., or at a temperature as high as about 180° C., about 190° C., about 200° C., about 210° C., about 220° C., about 230° C., about 240° C., or about 250° C., or within any range defined between any two of the foregoing values, such as about 100° C. to about 250° C., about 110° C. to about 240° C., about 120° C. to about 230° C., about 130° C. to about 220° C., about 140° C. to about 210° C., about 150° C. to about 200° C., about 160° C. to about 190° C., about 170° C. to about 180° C., about 120° C. to about 130° C., about 110° C. to about 180° C., or about 120° C. to about 250° C., or within any range defined between any two of the foregoing values, such as about 100° C. to about 250° C., about 110° C. to about 240° C., about 120° C. to about 230° C., about 130° C. to about 220° C., about 140° C. to about 210° C., about 150° C. to about 200° C., about 160° C. to about 190° C., about 170° C. to about 180° C., about 120° C. to about 130° C., about 110° C. to about 180° C., or about 120° C. to about 250° C., for example. Preferably, the reactants are heated to a temperature from about 100° C. to about 250° C. More preferably, the reactants are heated to a temperature from about 110° C. to about 200° C. Most preferably, the reactants are heated to a temperature of about 120° C. to about 190° C.

Pressure is not critical. Convenient operating pressures range from about 10 KPa to about 4,000 KPa, and preferably around ambient pressure, or about 100 KPa to about 250 KPa.

The reaction is carried out in a liquid phase reactor. The liquid phase reactor may be a semi-batch or continuously stirred tank reactor (CSTR). The reaction may be carried out as a batch process or as a continuous process.

The volatile products of the reaction, including the trifluoroiodomethane, may be condensed and collected, thus separating the trifluoroiodomethane from the non-volatile metal iodide byproduct.

The composition of the volatile organic products of the reaction may be measured by gas chromatography (GC) and gas chromatography-mass spectroscopy (GC-MS) analyses. Graph areas provided by the GC analysis for each of the volatile organic compounds may be combined to provide a GC area percentage (GC area %) of the total volatile organic compounds for each of the volatile organic compounds as a measurement of the relative concentrations of the volatile organic compounds produced in the reaction.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Example 1

Decarboxylative Iodination of $CF_3COOM$ without Catalyst

In this Example, the manufacture of trifluoroiodomethane from potassium trifluoroacetate ($CF_3COOK$) and elemental iodine is demonstrated for comparison purposes. Potassium trifluoroacetate in an amount of 20 g and elemental iodine in an amount of 38 g were added to a 300-mL reactor from Parr Instrument Company, Moline, Ill. The reactor was equipped with a condenser. The reactor was pressure tested to 300 psig, and then evacuated. Sulfolane in an amount of 60 mL was added to the reactor to form a reactant mixture having a mole ratio of potassium trifluoroacetate to elemental iodine of about 0.88:1. The reactants and the solvent were obtained from Sigma-Aldrich Corp., St. Louis, Mo. and used without further purification.

The reactant mixture was heated to about 175° C. No phase transfer catalyst or metal catalyst was used in the reaction. Volatile gaseous products and byproducts were produced as the reaction proceeded. The pressure in the reactor was measured as the reaction progressed. The pressure in the reactor over time is shown in the FIGURE. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

Example 2

Decarboxylative Iodination of $CF_3COOM$ Using Phase Transfer Catalysis

In this Example, the manufacture of trifluoroiodomethane from potassium trifluoroacetate ($CF_3COOK$) and iodine ($I_2$) according to Equation 1 described above is demonstrated. Potassium trifluoroacetate in an amount of 20 g, tetraphenylphosphonium bromide (TPPB) in an amount of 13.8 g (25 mol %) and iodine ($I_2$) in an amount of 36.7 g were added to a 300 mL reactor from Parr Instrument Company, Moline, Ill. The reactor was equipped with a condenser. The reactor was pressure tested to 300 psig, and then evacuated. Sulfolane in an amount of 60 mL of sulfolane was added to the reactor to form a reactant mixture having a mole ratio of potassium trifluoroacetate to elemental iodine of about 0.91:1. The reactants and the solvent were obtained from Sigma-Aldrich Corp., St. Louis, Mo. and used without further purification. The phase transfer catalyst was obtained from Sigma-Aldrich Corp., St. Louis, Mo. and used without further purification. The reactant mixture was heated to about 175° C. Volatile gaseous products and byproducts were produced as the reaction proceeded. The pressure in the reactor was measured as the reaction progressed. The pressure in the reactor over time is shown in the FIGURE. The volatile gases exiting the condenser were collected in a product collection cylinder cooled in dry ice.

The composition of the organic compounds in the volatile gases collected in the product collection cylinder was measured by gas chromatography (GC). Graph areas provided by the GC analysis for each of the organic compounds were combined to provide a GC area percentage (GC area %) of the total organic compounds for each of the organic compounds as a measurement of the relative concentrations of the organic compounds. The results are shown in the Table below.

As shown in the Table below, the use of phase transfer catalysis results in higher selectivity for trifluoroiodomethane with reduced production of the byproduct trifluoromethane ($CHF_3$) when compared to the reaction in the absence of phase transfer catalysis. As shown in the FIGURE, the use phase transfer catalysis also results in significantly reduced reaction time. The formation of $CHF_3$ is attributed to the presence of moisture in the reaction vessel.

TABLE

| Phase transfer catalyst | $CF_3I$ (GC area %) | $CHF_3$ (GC area %) | Other (GC area %) |
| --- | --- | --- | --- |
| none | 62.85% | 35.35% | 1.79% |
| TPPB | 63.17% | 30.84% | 5.99% |

ASPECTS

Aspect 1 is a process for producing trifluoroiodomethane ($CF_3I$), the process comprising providing a metal trifluoroacetate, iodine, a phase transfer catalyst, and an organic solvent; and reacting the metal trifluoroacetate and iodine in the presence of the phase transfer catalyst and the organic solvent to produce trifluoroiodomethane.

Aspect 2 is the process of Aspect 1, wherein in the providing step, the phase transfer catalyst is provided for the reaction at a mole percent of the metal trifluoroacetate from about 0.5% to about 50%.

Aspect 3 is the process of Aspect 1, wherein in the providing step, the phase transfer catalyst is provided for the reaction at a mole percent of the metal trifluoroacetate from about 0.5% to about 35%.

Aspect 4 is the process of Aspect 1, wherein in the providing step, the phase transfer catalyst is provided for the reaction at a mole percent of the metal trifluoroacetate from about 10% to about 30%.

Aspect 5 is the process of Aspect 1, wherein in the providing step, the phase transfer catalyst is provided for the reaction at a mole percent of the metal trifluoroacetate from about 20% to about 30%.

Aspect 6 is the process of any of Aspects 1-5, wherein in the providing step, the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

Aspect 7 is the process of any of Aspects 1-5, wherein in the providing step, the metal trifluoroacetate is at least one selected from the group of lithium trifluoroacetate, potassium trifluoroacetate, sodium trifluoroacetate, rubidium trifluoroacetate, and cesium trifluoroacetate.

Aspect 8 is the process of any of Aspects 1-5, wherein in the providing step, the metal trifluoroacetate is at least one selected from the group of potassium trifluoroacetate and sodium trifluoroacetate.

Aspect 9 is the process of any of Aspects 1-5, wherein in the providing step, the metal trifluoroacetate consists of potassium trifluoroacetate.

Aspect 10 is the process any of Aspects 1-9, wherein in the providing step, the organic solvent comprises less than about 500 ppm by volume of water.

Aspect 11 is the process any of Aspects 1-9, wherein in the providing step, the organic solvent comprises less than about 100 ppm by volume of water.

Aspect 12 is the process any of Aspects 1-9, wherein in the providing step, the organic solvent comprises less than about 50 ppm by volume of water.

Aspect 13 is the process any of Aspects 1-9, wherein in the providing step, the organic solvent comprises less than about 10 ppm by volume of water.

Aspect 14 is the process of any of Aspects 1-13, wherein in the providing step, the organic solvent is at least one selected from the group of an ionic liquid and a polar aprotic solvent.

Aspect 15 is the process of Aspect 14, wherein the organic solvent is at least one selected from the group of imidazolium salts, caprolactamium hydrogen sulfate, sulfolane, N,N-dimethylformamide, N,N-dimethylacetamide, acetonitrile, benzonitrile, N-methyl-2-pyrrolidone, and dimethyl sulfone.

Aspect 16 is the process of Aspect 15, wherein the organic solvent consists of sulfolane.

Aspect 17 is the process of any of Aspects 1-16, wherein in the providing step, the phase transfer catalyst is at least one selected from the group of quaternary ammonium salts and quaternary phosphonium salts.

Aspect 18 is the process of Aspect 17, wherein the phase transfer catalyst comprises tetraphenylphosphonium bromide.

Aspect 19 is the process of any of Aspects 1-18, wherein in the providing step, a mole ratio of metal trifluoroacetate to iodine is from about 0.1:1 to about 2.0:1.

Aspect 20 is the process of any of Aspects 1-18, wherein in the providing step, a mole ratio of metal trifluoroacetate to iodine is from about 0.8:1 to about 1.5:1.

Aspect 21 is the process of any of Aspects 1-18, wherein in the providing step, a mole ratio of metal trifluoroacetate to iodine is from about 1:1 to about 1.2:1.

Aspect 22 is the process of any of Aspects 1-21, wherein in the reacting step, the metal trifluoroacetate, the iodine, the phase transfer catalyst, and the organic solvent are at a temperature from about 100° C. to about 250° C.

Aspect 23 is the process of any of Aspects 1-21, wherein in the reacting step, the metal trifluoroacetate, the iodine, the phase transfer catalyst, and the organic solvent are at a temperature from about 110° C. to about 200° C.

Aspect 24 is the process of any of Aspects 1-21, wherein in the reacting step, the metal trifluoroacetate, the iodine, the phase transfer catalyst, and the organic solvent are at a temperature from about 120° C. to about 190° C.

Aspect 25 is a process for producing trifluoroiodomethane ($CF_3I$), the process comprising mixing a metal trifluoroacetate, iodine, a phase transfer catalyst, and an organic solvent; and heating the metal trifluoroacetate, iodine, the phase transfer catalyst, and the organic solvent to react the metal trifluoroacetate and iodine to produce trifluoroiodomethane and a metal iodide.

Aspect 26 is the process of Aspect 25, further including separating the trifluoroiodomethane from the metal iodide.

Aspect 27 is the process of either of Aspects 25 or 26, wherein the process is a continuous process.

Aspect 28 is the process of either of Aspects 25 or 26, wherein the process is a batch process.

Aspect 29 is the process of any of Aspects 25-28, wherein the phase transfer catalyst is provided for the reaction at a mole percent of the metal trifluoroacetate from about 0.5% to about 50%.

Aspect 30 is the process of any of Aspects 25-28, wherein the phase transfer catalyst is provided for the reaction at a mole percent of the metal trifluoroacetate from about 0.5% to about 35%.

Aspect 31 is the process of any of Aspects 25-28, wherein the phase transfer catalyst is provided for the reaction at a mole percent of the metal trifluoroacetate from about 10% to about 30%.

Aspect 32 is the process of any of Aspects 25-28, wherein the phase transfer catalyst is provided for the reaction at a mole percent of the metal trifluoroacetate from about 20% to about 30%.

Aspect 33 is the process of any of Aspects 25-32, wherein the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

Aspect 34 is the process of any of Aspects 25-32, wherein the metal trifluoroacetate is at least one selected from the group of lithium trifluoroacetate, potassium trifluoroacetate, sodium trifluoroacetate, rubidium trifluoroacetate, and cesium trifluoroacetate.

Aspect 35 is the process of any of Aspects 25-32, wherein the metal trifluoroacetate is at least one selected from the group of potassium trifluoroacetate, and sodium trifluoroacetate.

Aspect 36 is the process of any of Aspects 25-32, wherein the metal trifluoroacetate consists of potassium trifluoroacetate.

Aspect 37 is the process any of Aspects 25-36, wherein the organic solvent comprises less than about 500 ppm by volume of water.

Aspect 38 is the process any of Aspects 25-36, wherein the organic solvent comprises less than about 100 ppm by volume of water.

Aspect 39 is the process any of Aspects 25-36, wherein the organic solvent comprises less than about 50 ppm by volume of water.

Aspect 40 is the process any of Aspects 25-36, wherein the organic solvent comprises less than about 10 ppm by volume of water.

Aspect 41 is the process of any of Aspects 25-40, the organic solvent is at least one selected from the group of an ionic liquid and a polar aprotic solvent.

Aspect 42 is the process of Aspect 41, wherein the organic solvent is at least one selected from the group of imidazolium salts, caprolactamium hydrogen sulfate, sulfolane, N,N-dimethylformamide, N,N-dimethylacetamide, acetonitrile, benzonitrile, N-methyl-2-pyrrolidone, and dimethyl sulfone.

Aspect 43 is the process of Aspect 42, wherein the organic solvent consists of sulfolane.

Aspect 44 is the process of any of Aspects 25-43, wherein the phase transfer catalyst is at least one selected from the group of quaternary ammonium salts and quaternary phosphonium salts.

Aspect 45 is the process of Aspect 44, wherein the phase transfer catalyst comprises tetraphenylphosphonium bromide.

Aspect 46 is the process of any of Aspects 25-45, wherein a mole ratio of metal trifluoroacetate to iodine is from about 0.1:1 to about 2.0:1.

Aspect 47 is the process of any of Aspects 25-45, wherein a mole ratio of metal trifluoroacetate to iodine is from about 0.8:1 to about 1.5:1.

Aspect 48 is the process of any of Aspects 25-45, wherein a mole ratio of metal trifluoroacetate to iodine is from about 1:1 to about 1.2:1.

Aspect 49 is the process of any of Aspects 25-48, wherein the metal trifluoroacetate, the iodine, the phase transfer catalyst, and the organic solvent are heated to a temperature from 100° C. to 250° C.

Aspect 50 is the process of any of Aspects 25-48, wherein the metal trifluoroacetate, the iodine, the phase transfer catalyst, and the organic solvent are heated to a temperature from about 110° C. to about 200° C.

Aspect 51 is the process of any of Aspects 25-48, wherein the metal trifluoroacetate, the iodine, the phase transfer catalyst, and the organic solvent are heated to a temperature from about 120° C. to about 190° C.

What is claimed is:

1. A process for producing trifluoroiodomethane ($CF_3I$), the process comprising:
   providing a metal trifluoroacetate, iodine, a phase transfer catalyst, and an organic solvent; and
   reacting the metal trifluoroacetate and iodine in the presence of the phase transfer catalyst and the organic solvent to produce trifluoroiodomethane.

2. The process of claim 1, wherein in the providing step, the phase transfer catalyst is provided for the reaction at a mole percent of the metal trifluoroacetate from about 0.5% to about 50%.

3. The process of claim 1, wherein in the providing step, the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

4. The process of claim 1, wherein in the providing step, the organic solvent comprises less than about 500 ppm by volume of water.

5. The process of claim 1, wherein in the providing step, the organic solvent is at least one selected from the group of an ionic liquid and a polar aprotic solvent.

6. The process of claim 5, wherein the organic solvent is at least one selected from the group of imidazolium salts, caprolactamium hydrogen sulfate, sulfolane, N,N-dimethylformamide, N,N-dimethylacetamide, acetonitrile, benzonitrile, N-methyl-2-pyrrolidone, and dimethyl sulfone.

7. The process of claim 6, wherein the organic solvent consists of sulfolane.

8. The process of claim 1, wherein in the providing step, the phase transfer catalyst is at least one selected from the group of quaternary ammonium salts and quaternary phosphonium salts.

9. The process of claim 8, wherein the phase transfer catalyst comprises tetraphenylphosphonium bromide.

10. The process of claim 1, wherein in the reacting step, the metal trifluoroacetate, the iodine, the phase transfer catalyst, and the organic solvent are at a temperature from about 100° C. to about 250° C.

11. A process for producing trifluoroiodomethane ($CF_3I$), the process comprising:
   mixing a metal trifluoroacetate, iodine, a phase transfer catalyst, and an organic solvent; and
   heating the metal trifluoroacetate, iodine, the phase transfer catalyst, and the organic solvent to react the metal trifluoroacetate and iodine to produce trifluoroiodomethane and a metal iodide.

12. The process of claim 11, further including separating the trifluoroiodomethane from the metal iodide.

13. The process of claim 11, wherein the process is a continuous process.

14. The process of claim 11, wherein the process is a batch process.

15. The process of claim 11, wherein the metal trifluoroacetate is at least one selected from the group of lithium trifluoroacetate, potassium trifluoroacetate, sodium trifluoroacetate, rubidium trifluoroacetate, cesium trifluoroacetate, calcium trifluoroacetate, magnesium trifluoroacetate, iron trifluoroacetate, zinc trifluoroacetate, and copper trifluoroacetate.

16. The process of claim 11, wherein the organic solvent is at least one selected from the group of an ionic liquid and a polar aprotic solvent.

17. The process of claim 16, wherein the organic solvent is at least one selected from the group of imidazolium salts, caprolactamium hydrogen sulfate, sulfolane, N,N-dimethylformamide, N,N-dimethylacetamide, acetonitrile, benzonitrile, N-methyl-2-pyrrolidone, and dimethyl sulfone.

18. The process of claim 11, wherein the phase transfer catalyst is at least one selected from the group of quaternary ammonium salts and quaternary phosphonium salts.

19. The process of claim 11, wherein the phase transfer catalyst comprises tetraphenylphosphonium bromide.

20. The process of claim 11, wherein the metal trifluoroacetate, the iodine, phase transfer catalyst, and the organic solvent are heated to a temperature from about 100° C. to about 250° C.

* * * * *